(12) United States Patent
Shigeki

(10) Patent No.: US 9,895,326 B2
(45) Date of Patent: Feb. 20, 2018

(54) TOPICAL ORAL COMPOSITION FOR ALLEVIATING DRY MOUTH SYMPTOMS AND FOR TREATING MOUTH ULCERS

(71) Applicant: SUNSTAR SUISSE SA, Etoy (CH)

(72) Inventor: Mori Shigeki, Etoy (CH)

(73) Assignee: SUNSTAR SUISSE SA, Etoy (CH)

( * ) Notice: Subject to any disclaimer, the term of this patent is extended or adjusted under 35 U.S.C. 154(b) by 0 days.

(21) Appl. No.: 14/652,126

(22) PCT Filed: Dec. 10, 2013

(86) PCT No.: PCT/EP2013/076080
§ 371 (c)(1),
(2) Date: Jun. 15, 2015

(87) PCT Pub. No.: WO2014/095489
PCT Pub. Date: Jun. 26, 2014

(65) Prior Publication Data
US 2015/0320701 A1 Nov. 12, 2015

(30) Foreign Application Priority Data
Dec. 18, 2012 (EP) .................................. 12197696

(51) Int. Cl.
| | |
|---|---|
| *A61Q 11/00* | (2006.01) |
| *A61K 8/34* | (2006.01) |
| *A61K 9/00* | (2006.01) |
| *A61K 31/047* | (2006.01) |
| *A61K 31/145* | (2006.01) |
| *A61K 8/46* | (2006.01) |
| *A61K 31/185* | (2006.01) |
| *A61K 31/194* | (2006.01) |
| *A61K 31/205* | (2006.01) |
| *A61K 31/728* | (2006.01) |
| *A61K 33/16* | (2006.01) |
| *A61K 33/42* | (2006.01) |
| *A61K 8/24* | (2006.01) |
| *A61K 8/73* | (2006.01) |
| *A61K 8/19* | (2006.01) |
| *A61K 47/10* | (2017.01) |
| *A61K 47/12* | (2006.01) |
| *A61K 47/32* | (2006.01) |
| *A61K 47/36* | (2006.01) |
| *A61K 47/18* | (2017.01) |

(52) U.S. Cl.
CPC .............. *A61K 31/145* (2013.01); *A61K 8/19* (2013.01); *A61K 8/24* (2013.01); *A61K 8/345* (2013.01); *A61K 8/466* (2013.01); *A61K 8/735* (2013.01); *A61K 9/006* (2013.01); *A61K 31/047* (2013.01); *A61K 31/185* (2013.01); *A61K 31/194* (2013.01); *A61K 31/205* (2013.01); *A61K 31/728* (2013.01); *A61K 33/16* (2013.01); *A61K 33/42* (2013.01); *A61K 47/10* (2013.01); *A61K 47/12* (2013.01); *A61K 47/32* (2013.01); *A61K 47/36* (2013.01); *A61Q 11/00* (2013.01); *A61K 47/183* (2013.01); *A61K 2800/70* (2013.01)

(58) Field of Classification Search
USPC .................. 424/49, 52, 54; 514/574, 665
See application file for complete search history.

(56) References Cited

U.S. PATENT DOCUMENTS

| | | | | |
|---|---|---|---|---|
| 5,989,526 A | * | 11/1999 | Aaslyng | A61Q 11/00 424/49 |
| 2006/0140881 A1 | * | 6/2006 | Xu | A61K 8/345 424/49 |
| 2009/0104128 A1 | | 4/2009 | Haley | |
| 2010/0022471 A1 | | 1/2010 | Hanifl et al. | |
| 2010/0028318 A1 | * | 2/2010 | Saito | A23L 1/30 514/1.1 |

FOREIGN PATENT DOCUMENTS

| | | |
|---|---|---|
| EP | 0413427 | 2/1991 |
| WO | 2007136586 | 11/2007 |
| WO | 2010121081 | 10/2010 |

OTHER PUBLICATIONS

International Search Report and Written Opinion of PCT/EP2013/076080 of Feb. 27, 2014.

* cited by examiner

*Primary Examiner* — Lezah Roberts
(74) *Attorney, Agent, or Firm* — Silvia Salvadori, P.C.; Salvia Salvadori

(57) ABSTRACT

The invention concerns a topical oral composition comprising taurine, propanediol and xylitol and its use for alleviating or eliminating symptoms of dry mouth and/or preventing or treating mouth ulcers.

14 Claims, No Drawings

TOPICAL ORAL COMPOSITION FOR ALLEVIATING DRY MOUTH SYMPTOMS AND FOR TREATING MOUTH ULCERS

This applicatin is a U.S. natinal stage of PCT/EP2013/076080 filed on 10 Dec. 2013, which claims priority to and the benefit of European Application No. 1219869.3 filed on 18 Dec. 2012, the contents of which are incorporated herein by reference in their entireties.

FIELD OF THE INVENTION

The invention concerns a topical oral composition comprising taurine, propanediol and xylitol and its use for alleviating or eliminating symptoms of dry mouth and/or preventing or treating mouth ulcers.

TECHNOLOGICAL BACKGROUND

Dry mouth or xerostomia is caused by a decrease in the activity of salivary glands. The reduction of the salivary flow can result in discomfort, interfere with speech and swallowing, make wearing dentures difficult, cause halitosis, and impair oral hygiene by causing a decrease in oral pH and an increase in bacterial growth. Longstanding dry mouth can result in severe tooth decay and oral candidiasis. Dry mouth is a common complaint among older adults, affecting about 20% of the elderly.

The causes of dry mouth are different and involve many factors such as stress, infection of salivary glands or the use of drugs such as anticholinergics, antiparkinsonians, antineoplastics, radiation to the head and neck (for cancer treatment) or it may be also associated to certain diseases such as Sjögren's syndrome and HIV/AIDS, uncontrolled diabetes, and other disorders.

Dry mouth is currently treated with mouth rinses, topical applications, salivary substitutes, or salivary stimulants such as sugarless candies and chewing gum. Some saliva stimulants are commercially available. The current treatments focus on relieving the symptoms and preventing dental cavities. Artificial saliva products are often the treatment of choice for xerostomia patients.

Dry mouth can make oral soft tissues such as oral mucous membrane, gingival tissue and taste buds on tongue more vulnerable to damage physically, physicochemically and biologically. However existing treatments/products does not solve the problem of soft tissue trouble. The present compositions solve this problem due to the effect of protection and repair promotion of the oral soft tissues.

Mouth ulcers and oral lesions are inflammatory forms which occur on the oral mucosa with erythematous lesions similar to burns and injuries, such painful ulcers making it difficult chewing and swallowing, compromising the quality of life of the patient. They are painful because a layer of the oral mucosa has been removed, exposing the nerve endings beneath.

There are a number of various causes, including poor-fitting braces and dentures, physical or chemical trauma, dry mouth, taking immuno-suppressive medications, burns, allergies, infection from microorganisms or viruses. Once formed, the ulcer may be maintained by inflammation and/or secondary infection. Two common oral ulcer types are aphthous ulcers (canker sores) and cold sores. Cold sores can be caused by the herpes simplex virus.

Mouth ulcers are managed with topical rinses, topical gels and liquids, behavioural modifications, analgesics and preventive measures.

DESCRIPTION OF THE INVENTION

In accord with the present invention it has been found that compositions containing taurine, xylitol and propane-1,3-diol, topically applied to the mucous membrane of the mouth, exert beneficial effects on dry mouth and promote regeneration of oral mucous membrane.

The present invention provides topical oral compositions comprising taurine or a salt thereof, xylitol and propane-1,3-diol.

Taurine (2-aminoethanesulfonic acid) is an organic acid widely distributed in animal tissues. Taurine is present in high concentration in mammalian plasma and cells and plays an important role in a number of biological processes. Taurine has been shown to have osmoregulatory, antioxidative, antiapoptopic, anti-inflammatory and antilipidic activity.

Xylitol is classified as a polyol and it is considered a "sugar-free" sweetener. Xylitol is known to reduce the risk of tooth decay.

Propane-1,3-diol is commercialized under the trademark Zemea® and it is known to be an emollient, humectant, hand-feel modifier or solvent.

The composition of the present invention are able to protect oral soft tissues and promote their repair, to relieve inflammation of oral soft tissues, to prevent taste disorder due to protection of taste buds and to protect from dryness damage due to humectant function.

The concentration of taurine in the composition varies from 0.01 to 5.0% by weight, preferably the concentration is 0.1 to 1.0% by weight.

The concentration of xylitol in the composition varies from 0.1 to 10.0% by weight, preferably the concentration is 0.5 to 5.0% by weight.

The concentration of propone-1,3-diol in the composition varies from 0.1 to 30.0% by weight, preferably the concentration is 2.0 to 20.0% by weight.

The composition may further comprise sodium hyaluronate.

Sodium hyaluronate is present in a concentration of 0.01 to 1.0% by weight, preferably the concentration is 0.05 to 0.3% by weight. Sodium hyaluronate has preferably a Molecular Weight (MW) of $1.0\text{-}1.5 \times 10^6$.

The compositions of the invention may comprise further components such as remineralizing agents, osmoprotectant agents, lubricating agents, compounds for stimulating saliva flow.

Remineralising agents preferably are chosen among fluoride anions, phosphate anions, sodium cations and potassium cations such as potassium fluoride, sodium fluoride, sodium monofluorophosphate, tin fluoride, amine fluorides (hexadecylamine hydrofluoride, bis-(hydroxyethyl)aminopropyl-N-hydroxyethyl-octadecylamine dihydrofluoride, N-N',N'-tri(polyoxyethylene)-N-hexadecyl-propylenediamine dihydrofluoride or octadecenylamine hydrofluoride), potassium phosphate, potassium pyrophosphate, tripotassium citrate, calcium lactate, calcium pantothenate and calcium carbonate.

Preferred remineralizing agent is sodium monofluorophosphate which is preferably present in concentrations of 0.10 to 1.14% by weight.

The osmoprotectant agent is preferably betaine, which is preferably present in concentrations of 0.5 to 5.0% by weight.

The preferred lubricating agent is polyvinylpyrrolidone, which is preferably is present in concentrations of 0.01 to 5.0% by weight.

The compound for stimulating saliva flow may be a citrate salt or citric acid. The preferred compound for stimulating saliva flow is citrate sodium/citric acid which is preferably present in concentrations of 0.5 to 5.0% by weight. The composition of the invention can include at each time all the necessary ingredients known to the skilled in the art in order to obtain the necessary organoleptic and rheologic properties.

The topical oral composition according to claims may be in the form of gel, spray, toothpaste, mouthwash, oral patch, chewing gum and tablet.

EXAMPLES

Example 1

| Dry mouth gel | |
|---|---|
| INCI-EU NAMES | % |
| AQUA | 49.583969 |
| SORBITOL, AQUA | 25.000000 |
| PROPANEDIOL | 15.000000 |
| PVP | 3.000000 |
| SODIUM CITRATE | 2.400000 |
| BETAINE | 1.000000 |
| GLUCONOLACTONE, SODIUM BENZOATE, CALCIUM GLUCONATE | 1.000000 |
| CARRAGEENAN | 0.700000 |
| XANTHAN GUM | 0.700000 |
| XYLITOL | 0.500000 |
| PEG-40 HYDROGENATED CASTOR OIL | 0.400000 |
| TAURINE | 0.300000 |
| CITRIC ACID | 0.240000 |
| SODIUM HYDROXIDE | 0.076000 |
| SODIUM HYALURONATE | 0.050000 |
| SUCRALOSE | 0.030000 |
| STEVIA REBAUDIANA EXTRACT | 0.010000 |
| CI 19140 | 0.000026 |
| CI 42090 | 0.000005 |
| total | 100.000000 |

Example 2

| Dry mouth toothpaste | |
|---|---|
| INCI-EU NAMES | % |
| SORBITOL, AQUA | 43.000000 |
| AQUA | 15.843000 |
| PROPANEDIOL | 10.000000 |
| SILICA | 13.500000 |
| BETAINE | 4.000000 |
| LAURYL GLUCOSIDE | 3.000000 |
| COCAMIDOPROPYL BETAINE, AQUA | 2.000000 |
| XANTHUM GUM | 1.500000 |
| POLYSORBATE 20 | 1.500000 |
| SODIUM CITRATE | 1.200000 |
| SODIUM MONOFLUOROPHOSPHATE | 1.097000 |
| XYLITOL | 1.000000 |
| GLUCONOLACTONE, SODIUM BENZOATE, CALCIUM GLUCONATE | 0.800000 |
| AROMA | 0.500000 |
| CI77891 | 0.400000 |
| TAURINE | 0.300000 |
| STEVIA REBAUDIANA EXTRACT | 0.100000 |
| SUCRALOSE | 0.100000 |
| CITRIC ACID | 0.100000 |
| SODIUM HYALURONATE | 0.050000 |
| PVP | 0.010000 |
| total | 100.000000 |

Example 3

| Dry mouth mouthwash | |
|---|---|
| INCI-EU NAMES | % |
| AQUA | 79.480000 |
| SORBITOL, AQUA | 10.000000 |
| SODIUM CITRATE | 2.400000 |
| PVP | 2.000000 |
| PROPANEDIOL | 2.000000 |
| BETAINE | 1.000000 |
| GLUCONOLACTONE, SODIUM BENZOATE, CALCIUM GLUCONATE | 1.000000 |
| PEG-40 HYDROGENATED CASTOR OIL | 0.600000 |
| XYLITOL | 0.500000 |
| TAURINE | 0.300000 |
| CITRIC ACID | 0.240000 |
| SODIUM MONOFLUOROPHOSPHATE | 0.190000 |
| SODIUM HYDROXIDE | 0.100000 |
| AROMA | 0.090000 |
| SODIUM HYALURONATE | 0.050000 |
| HYDROXYETHYLCELLULOSE | 0.020000 |
| SUCRALOSE | 0.020000 |
| STEVIA REBAUDIANA EXTRACT | 0.010000 |
| total | 100.000000 |

Example 4

| Dry mouth spray | |
|---|---|
| INCI-EU NAMES | % |
| AQUA | 79.560000 |
| SORBITOL, AQUA | 10.000000 |
| SODIUM CITRATE | 2.300000 |
| PVP | 2.000000 |
| PROPANEDIOL | 2.000000 |
| BETAINE | 1.000000 |
| GLUCONOLACTONE, SODIUM BENZOATE, CALCIUM GLUCONATE | 1.000000 |
| PEG-40 HYDROGENATED CASTOR OIL | 1.000000 |
| XYLITOL | 0.500000 |
| TAURINE | 0.300000 |
| CITRIC ACID | 0.240000 |
| SODIUM HYALURONATE | 0.050000 |
| SUCRALOSE | 0.030000 |
| STEVIA REBAUDIANA EXTRACT | 0.010000 |
| AROMA | 0.010000 |
| total | 100.000000 |

The invention claimed is:

1. A topical oral composition comprising taurine or a salt thereof, xylitol, propane-1,3-diol and betaine, wherein the concentration of taurine or a salt thereof is from 0.01 to 5.0% by weight, the concentration of xylitol is from 0.1 to 10.0% by weight, the concentration of propane-1,3 diol is from 0.1 to 30.0% by weight and the concentration of betaine is from 0.5 to 5.0%.

2. The topical oral composition of according to claim 1 further comprising sodium hyaluronate.

3. The topical oral composition of according to claim 1 further comprising a remineralizing agent.

4. The topical oral composition of claim 3 wherein the remineralizing agent is selected from the group consisting of fluoride anions, phosphate anions, sodium cations and potassium cations, sodium fluoride, sodium monofluorophosphate, tin fluoride, amine fluorides, potassium phosphate, potassium pyrophosphate, tripotassium citrate, calcium lactate, calcium pantothenate and calcium carbonate.

5. The topical oral composition of claim 4 wherein the remineralizing agent is sodium monofluorophosphate or sodium fluoride.

6. The topical oral composition of according to claim 1 further comprising a lubricating agent.

7. The topical oral composition according to claim 6 wherein the lubricating agent is polyvinylpyrrolidone.

8. The topical oral composition of claim 1 further comprising a compound for stimulating saliva flow.

9. The topical oral composition of claim 8 wherein the compound for stimulating saliva flow is a citrate salt or citric acid.

10. The topical oral composition of according to claim 1 in the form of gel, spray, toothpaste, mouthwash, oral patch, chewing gum and tablet.

11. Method for alleviating or eliminating the symptoms of dry mouth in a patient in need thereof said method comprising:

administering an effective amount of the topical oral composition according to claim 1 to said patient; and alleviating or eliminating said symptoms of dry mouth in said patient.

12. Method for preventing or treating oral ulcers in a patient in need thereof, said method comprising:

administering an effective amount of the topical oral composition according to claim 1 to said patient and preventing or treating said oral ulcers in said patient.

13. The topical oral composition according to claim 4, wherein the remineralizing agent is potassium fluoride.

14. The topical oral composition according to claim 4, wherein said amine fluorides comprise hexadecylamine hydrofluoride, bis-(hydroxyethyl)aminopropyl-N-hydroxyethyl-octadecylamine dihydrofluoride, N-N',N'-tri(polyoxyethylene)-N-hexadecyl-propylenediamine dihydrofluoride or octadecenylamine hydrofluoride.

* * * * *